(12) United States Patent
Mo et al.

(10) Patent No.: US 10,918,282 B2
(45) Date of Patent: Feb. 16, 2021

(54) EYE-EXAMINING APPARATUS IN WHICH VISIBLE-OPTICAL CHANNEL AND INFRARED-OPTICAL CHANNEL ARE INTEGRATED

(71) Applicant: HUVITZ CO., LTD., Anyang-si (KR)

(72) Inventors: Jae Hong Mo, Gunpo-si (KR); Min Soo Cho, Seoul (KR); Min Su Kim, Seoul (KR)

(73) Assignee: HUVITZ CO., LTD., Anyang-si (KR)

( * ) Notice: Subject to any disclaimer, the term of this patent is extended or adjusted under 35 U.S.C. 154(b) by 88 days.

(21) Appl. No.: 16/218,750

(22) Filed: Dec. 13, 2018

(65) Prior Publication Data

US 2019/0183340 A1 Jun. 20, 2019

(30) Foreign Application Priority Data

Dec. 18, 2017 (KR) .................. 10-2017-0174294

(51) Int. Cl.
*A61B 5/00* (2006.01)
*A61B 3/15* (2006.01)
(Continued)

(52) U.S. Cl.
CPC ............ *A61B 5/0035* (2013.01); *A61B 3/107* (2013.01); *A61B 3/156* (2013.01); *A61B 5/0075* (2013.01);
(Continued)

(58) Field of Classification Search
CPC ........... A61B 3/14; A61B 3/0025; A61B 3/12; A61B 3/102; A61B 3/0058; A61B 3/1225; A61B 3/0008; A61B 3/113; A61B 3/1025; A61B 3/145; A61B 3/0041; A61B 3/0091; A61B 3/103; A61B 3/1005; A61B 3/1015; A61B 3/117; A61B 3/112; A61B 3/107;
(Continued)

(56) References Cited

U.S. PATENT DOCUMENTS 5,844,660 A * 12/1998 Uchida .................. A61B 3/107
351/211
6,382,796 B1 5/2002 Ban
(Continued)

FOREIGN PATENT DOCUMENTS

JP H11-206709 8/1999
JP 2010-017279 1/2010

*Primary Examiner* — William R Alexander
*Assistant Examiner* — Sharrief I Broome
(74) *Attorney, Agent, or Firm* — Lex IP Meister, PLLC

(57) ABSTRACT

An eye-examining apparatus in which a visible light optical system for observing a shape of an examinee's eye and an infrared optical system for detecting a shape of the cornea of the examinee's eye are integrated. The eye-examining apparatus having an integrated optical system comprises: an infrared light source for irradiating a cornea of the examinee's eye with infrared light; a visible light source for irradiating the eye with visible light; an image detector both for detecting an image of the infrared light which is irradiated from the infrared light source and reflected from the cornea of the eye and for detecting an image of the visible light which is irradiated from the visible light source to the eye; and a visible light blocking filter inserted in an optical path of the visible light and the infrared light traveling toward the image detector for blocking the visible light.

6 Claims, 3 Drawing Sheets

(51) Int. Cl.
*A61B 3/107* (2006.01)
*A61B 5/107* (2006.01)

(52) U.S. Cl.
CPC ........... *A61B 5/0077* (2013.01); *A61B 5/1075* (2013.01); *A61B 2562/0233* (2013.01)

(58) Field of Classification Search
CPC .... A61B 3/13; A61B 3/0033; G01B 9/02091; G01B 9/02044; G01B 9/02004; G01B 9/02027; G01B 2290/45; G01B 2290/70; G01B 9/0203; G01B 9/02083; G01B 2290/65; G01B 9/02041; G01B 9/02087; G01B 1/2518; G01B 9/0201; G01B 9/0211; G01B 9/02028; G01B 9/02034; G01B 9/02039; G01B 9/02045; G01B 9/02048; G01B 9/0205; G06T 2207/30041; G06T 2207/10101; G06T 7/0012; G06T 2207/20056; G06T 2207/30104; G06T 5/50; G06T 7/0016; G06T 7/248; G06T 7/337; G06T 15/00; G06T 15/04; G06T 2207/10028; G06T 2207/10048; G06T 2207/10144; G06T 2207/20081; G06T 2207/30096; G06T 2207/30101; G06T 3/0018; G06T 3/0062; G06T 3/4053; G02B 27/141; G02B 26/101; G02B 27/0068; G02B 2027/0187; G02B 26/0833; G02B 27/1013; G02B 7/023; G02B 7/04; G02B 13/0095; G02B 17/006; G02B 17/08; G02B 17/0832; G02B 2027/0118; G02B 2027/0127; G02B 2027/0138; G02B 2027/014; G02B 2027/0178; G02B 2027/0185; G02B 21/0012; G02B 21/0048; A61F 9/007; A61F 2009/00851; A61F 2009/00897; A61F 9/00736; A61F 9/008; A61F 9/00821; A61F 2009/00863; A61F 2009/0087; A61F 2009/00887; A61F 2250/0002; A61F 2/1624; A61F 9/00814; A61F 9/00817; A61F 9/00823; A61F 9/00825; A61F 9/0084; A61F 9/009; A61F 9/013
See application file for complete search history.

(56) References Cited

U.S. PATENT DOCUMENTS

| | | | |
|---|---|---|---|
| 8,007,104 B2 | 8/2011 | Sekiguchi et al. | |
| 2004/0100570 A1* | 5/2004 | Shizukuishi | H04N 9/045 348/272 |
| 2008/0100801 A1* | 5/2008 | Yahagi | A61B 3/0033 351/206 |
| 2010/0238402 A1* | 9/2010 | Itoh | A61B 3/14 351/206 |
| 2010/0283970 A1* | 11/2010 | Sekiguchi | A61B 3/12 351/206 |
| 2011/0090457 A1* | 4/2011 | Shikaumi | A61B 3/14 351/206 |
| 2012/0069300 A1* | 3/2012 | Kakuuchi | A61B 3/14 351/206 |
| 2014/0347631 A1* | 11/2014 | Kishida | A61B 3/14 351/208 |

* cited by examiner

[Figure 1]
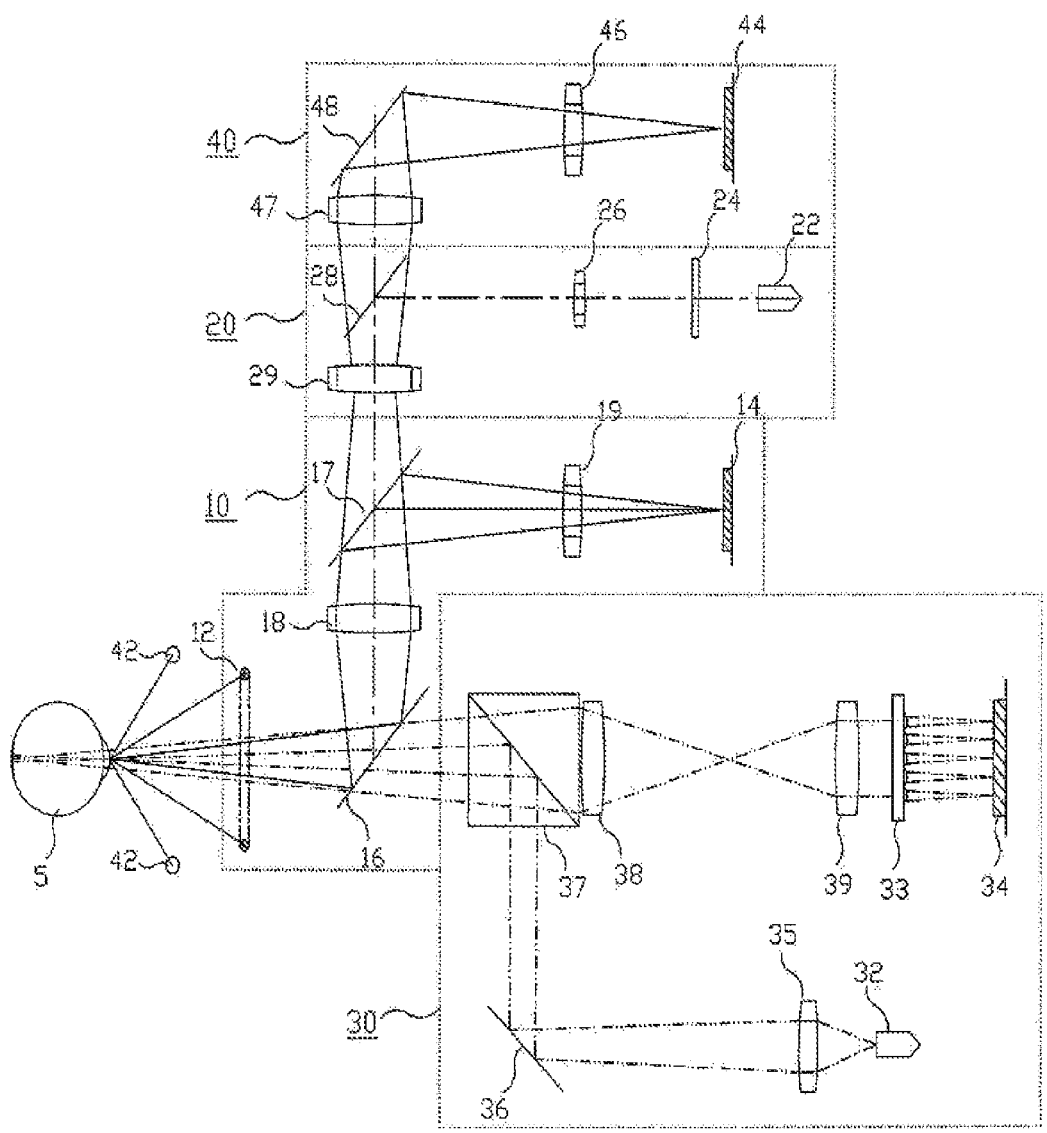

[Figure 2]
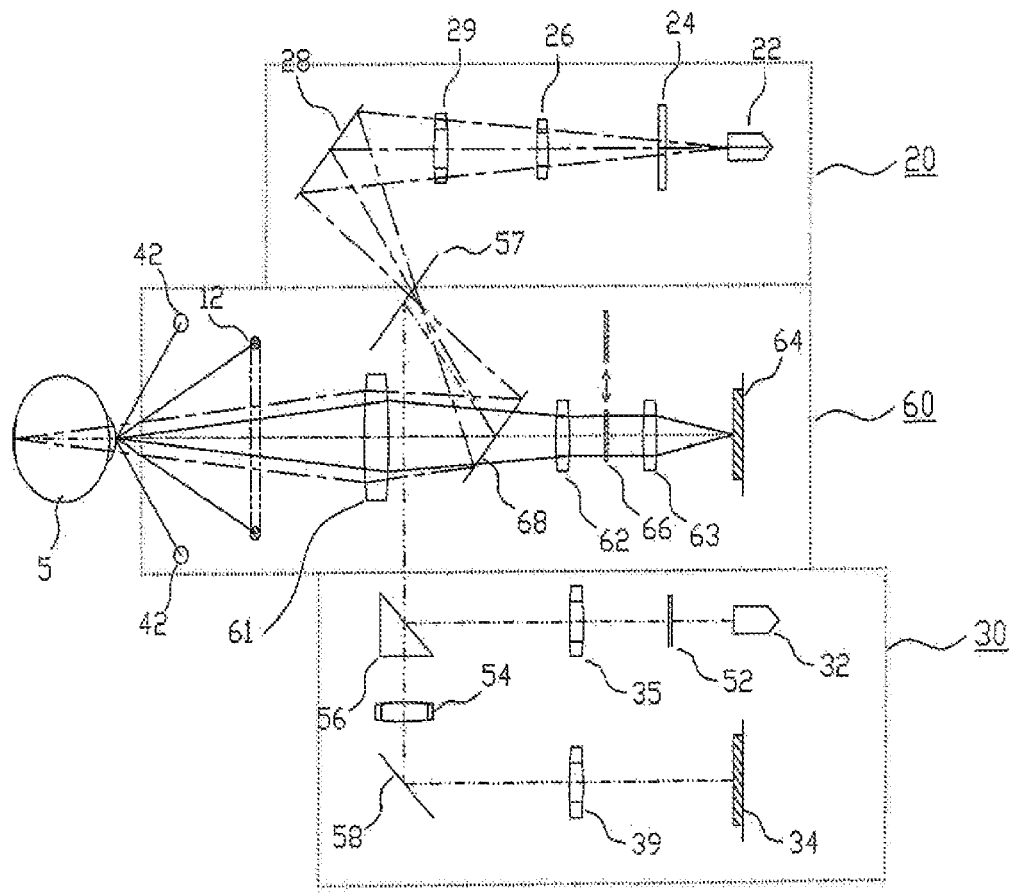
[Figure 3]

[Figure 4]
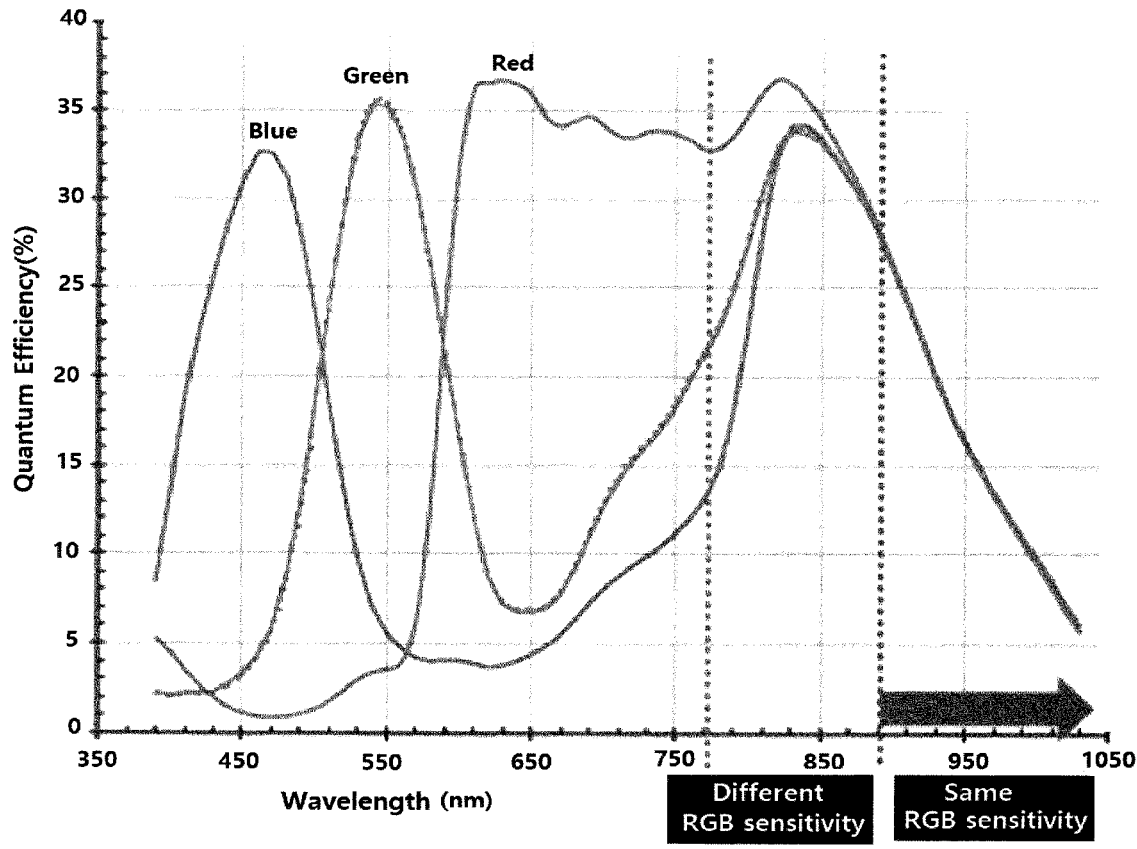
[Figure 5]
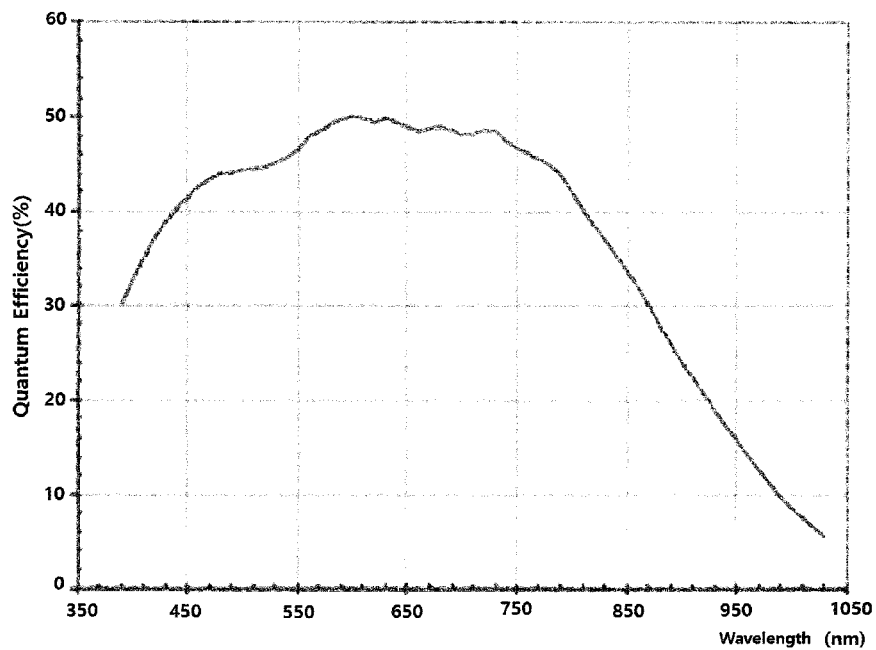

EYE-EXAMINING APPARATUS IN WHICH VISIBLE-OPTICAL CHANNEL AND INFRARED-OPTICAL CHANNEL ARE INTEGRATED

CROSS-REFERENCE TO RELATED APPLICATION

This application claims priority to Korean Patent Application No. 10-2017-0174294, filed on Dec. 18, 2017, the disclosures of which are incorporated herein by reference in its entirety.

FIELD OF THE INVENTION

The present invention relates to an eye-examining apparatus, and more particularly, to an eye-examining apparatus in which a visible-optical channel for observing a shape of an examinee's eye and an infrared-channel for detecting a configuration of the examinee's cornea are integrated.

BACKGROUND OF THE INVENTION

An eye-examining apparatus is a precise measuring-instrument used in the field of ophthalmic optics, in which optical equipment, electronic equipment, precise machines and computer programs are integrated. The eye-examining apparatus objectively measures physical features of an eye such as a refractive power, an astigmatism power, an astigmatism axis and so on, with optical and electronic systems. Thus, the eye-examining apparatus is generally used for a prescription of eyeglass or contact lens. FIG. 1 is an optical circuit diagram showing a configuration of a conventional automatic eye-examining apparatus. As shown in FIG. 1, the conventional eye-examining apparatus includes an infrared optical system (keratometer) 10 for detecting a configuration of the examinee's cornea, a chart optical system 20 for transmitting chart images to the examinee's eye, a measuring optical system (refractometer) 30 for measuring a refractive power of the examinee's eye and a color observing optical system (color channel) 40 for obtaining visible images of the examinee's eye for observing a shape of the eye (See: Korean patent application laid-open No. 10-2012-0090331).

The infrared optical system 10 includes an infrared light source 12 for emitting infrared light of mire ring to the examinee's cornea and an image detector 14 for detecting the mire ring image of infrared light reflected from the cornea of the examinee's eye 5 so that the corneal curvature and alignment state of the examinee's eye 5 are measured from the position and size of the ring-shaped infrared light detected by the image detector 14. If necessary, the infrared optical system 10 further includes first and second dichroic beam splitters 16 and 17 for reflecting and directing the mire ring infrared light to the image detector 14 and at least one relay lens 18, 19 for transmitting and/or focusing the mire ring infrared light.

The chart optical system 20 includes an illumination source 22 for emitting illumination light, a chart to which the illumination is transmitted to produce a chart image for fixing the eyes thereon, an adjustment lens 26 for adjusting a focal distance of the image produced in the chart 24, and a reflection mirror 28 and a relay lens 29 for transmitting the image generated in the chart 24 to the eye. Here, the chart image formation on the retina of the eye 5 is performed by adjusting the distance between the adjustment lens 26 and the chart 24 by moving the adjustment lens 26 and/or the chart 24. In operation of the chart optical system 20, from the illumination source 22 is emitted the white illumination light which in turn passes through the chart 24, thereby to generate a chart image for fixing the eyes 5 on the chart and for releasing the adjustment force of the eyes. The image generated in the chart 24 is passed through the adjustment lens 26, the third dichroic beam splitter 28 and the relay lens 29 which make a clear focus according to the refractive power of the eye 5 and then delivered to and focused on a retina of the examinee's eye 5.

The refractive power measuring optical system 30 includes a measuring light source 32 for emitting a light for measuring a refractive power of the examinee's eye 5, micro-lens array 33 for dividing the signal light formed by the measuring light reflected by the retina of the examinee's eye 5 and refracted at the eye 5 into a plurality of signal lights and then focusing the signal lights, and an image detector 34 for detecting images of the divided signal lights from which the refractive power of the examinee's eye 5 is calculated. If necessary, the measuring optical system 30 further includes a focusing lens 35 for focusing the measuring light on the eye 5, a reflection mirror 36 for reflecting the measuring light, a beam splitter 37 for directing the measuring light reflected to the eye 5, an objective lens 38 for focusing the signal light formed by reflecting the measuring light on the retina of the eye 5, an imaging lens 39 for converging the focused signal light, and the like.

The observing optical system 40 includes a light source 42 for emitting visible light to the examinee's eye 5 and an image detector 44 for detecting and obtaining an image of the examinee's eye 5 irradiated with visible light to observe the examinee's eye 5. The light source 42 may be a white light source emitting white light for observing the state of the examinee's eye 5 or a blue light source emitting blue light capable of tracking the position of the fluorescent substance by reacting with the fluorescent substance administered to the eye 5. The visible-light image of the eye 5 is transmitted to the image detector 44 through the first to third dichroic beam splitters 16, 17 and 18, the relay lenses 46 and 47 and the reflection mirror 48.

As shown in FIG. 1, the conventional eye-examining apparatus includes two infrared-optical channels of the infrared optical system 10 and the measuring optical system 30 each having respective image detector 14, 34 for sensing infrared light. Also, the eye-examining apparatus includes one visible-optical channel of the observing optical system 40 for observing the examinee's eye with color image, the image detector 44 being provided in the visible-optical channel. As the image detectors 14, 34 and 44, typical CMOS sensors can be used. The conventional eye-examining apparatus employs a separate image detector for each optical channel. Therefore, it has disadvantages that the number of components and the size of the eye-examining apparatus are increased, its manufacturing cost is relatively high, and its internal configuration is complicated to result in increasing possibility of malfunction and failure.

SUMMARY OF THE INVENTION

An object of the present invention is to provide an eye-examining apparatus whose components and size are reduced thereby to reduce its manufacturing cost. Another object of the present invention is to provide an eye-examining apparatus having simple internal configuration thereby to reduce possibility of malfunction and failure.

For achieving the above object, the present invention provides an eye-examining apparatus having a visible-infrared integrated optical system 60 comprising: an infrared light source 12 for irradiating a cornea of an examinee's eye 5 with infrared light of a predetermined shape; a visible light source 42 for irradiating the examinee's eye 5 with visible light; an image detector 64 for detecting an image of the infrared light which is irradiated from the infrared light source 12 and reflected from the cornea of the examinee's eye 5 and for detecting an image of the visible light which is irradiated from the visible light source 42 to the examinee's eye 5; and a visible light blocking filter 66 inserted in an optical path of the visible light and infrared light traveling toward the image detector 64 for blocking the visible light.

The eye-examining apparatus according to the present invention reduces the number of components and the size to down its manufacturing cost and has relatively simple internal configuration to reduce possibility of malfunction and failure.

BRIEF DESCRIPTION OF DRAWINGS

FIG. 1 is an optical circuit diagram showing a configuration of a conventional automatic eye-examining apparatus.

FIG. 2 is an optical circuit diagram showing a configuration of one embodiment of an eye-examining apparatus according to the present invention.

FIG. 3 is a diagram for explaining pixel structure of a color CMOS sensor used in the eye-examining apparatus according to the present invention.

FIG. 4 is a graph showing quantum efficiency according to wavelength of a color CMOS sensor used in the eye-examining apparatus according to the present invention.

FIG. 5 is a graph showing the quantum efficiency of a conventional monochromatic sensor.

DETAILED DESCRIPTION OF THE INVENTION

Hereinafter, the present invention will be described in detail with reference to the accompanying drawings. In the drawings, elements that perform the same or similar functions as the conventional ones are given the same reference numerals. FIG. 2 is an optical circuit diagram showing a configuration of one embodiment of an eye-examining apparatus according to the present invention As shown in FIG. 2, the eye-examining apparatus according to the present invention comprises a visible-infrared integrated optical system 60, and if necessary, further comprises a chart optical system 20 for transmitting chart images to the examinee's eye and a measuring optical system 30 for measuring a refractive power of the examinee's eye.

The visible-infrared integrated optical system 60 comprises an infrared light source 12 for irradiating the cornea of the examinee's eye 5 with infrared light of a predetermined shape, for example mire ring shape; a visible light source 42 for irradiating the examinee's eye 5 with visible light; an image detector 64 for detecting an image of the infrared light which is irradiated from the infrared light source 12 and reflected from the cornea of the examinee's eye 5 and for detecting an image of the visible light which is irradiated from the visible light source 42 to the examinee's eye 5; and a visible light blocking filter 66 inserted in an optical path of visible light and infrared light traveling toward the image detector 64 for blocking the visible light. The integrated optical system 60 is a system in which the infrared optical system (keratometry channel) and the observing optical system (color channel or image channel) are integrated. Therefore the infrared optical system and the observing optical system share one optical system and one detector 64 is used to selectively detect the visible light image or the infrared image, the infrared optical system being for measuring a corneal configuration of the examinee's eye 5 by detecting the image of infrared light reflected from the cornea of the examinee's eye 5, and the observing optical system being for obtaining the visible light image of the examinee's eye 5 to observe the shape of the examinee's eye 5. If necessary, the integrated optical system 60 further comprises an objective lens 61 for focusing or transmitting infrared light and visible light and one or more relay lenses 62, 63 for transmitting infrared light and visible light.

The cornea measuring process of the examinee's eye using the visible-infrared integrated optical system 60 is as follows. Infrared light having a predetermined shape is irradiated from the infrared light source 12 to the cornea of the examinee's eye 5. The visible light is cut off from the infrared light reflected by the cornea of the examinee's eye 5 with the visible light blocking filter 66. Then, the image of infrared light reflected at the cornea of the eye 5 is detected by the image detector 64. The cornea configuration is measured from the shape, size and so on of the infrared light image detected. On the other hand, the observing process of the image of the examinee's eye 5 using the integrated optical system 60 is as follows. In a state where the visible light blocking filter 66 is removed from the optical path of the visible light, the visible light from the visible light source 42 is irradiated to the examinee's eye 5 and then reflected from the examinee's eye 5 and then the visible light image of the eye 5 is detected at the image detector 64. The state of the examinee's eye 5 can be seen with the naked eye of the inspector. The movement of the visible light blocking filter 66 can be controlled by using a typical driving mechanism such as a motor and a typical detector such as a photo sensor.

In the integrated optical system 60, when the infrared optical system (keratometry channel) is employed (that is when infrared light is irradiated from the infrared light source 12), the visible light blocking filter 66 is inserted into the path of infrared light to cut off the visible light so that the infrared light image reflected by the cornea of the examinee's eye 5 is detected at the image detector 64. On the other hand, in the case of using the observing optical system (image channel) (that is when visible light is emitted from the visible light source 42), the visible light blocking filter 66 is removed from the path of visible light so that the visible light image of the examinee's eye 5 is detected at the image detector 64.

As the image detector 64 can be used a color sensor, and specifically color COMS sensor (complementary metal-oxide semiconductor sensor) can be used. The color sensor generates an electric signal according to the wavelength of the light incident thereon. FIG. 3 is a diagram for explaining pixel structure of a color CMOS sensor used in the eye-examining apparatus according to the present invention. As shown in FIG. 3, the color CMOS sensor used in the present invention contains R pixels for sensing Red light, G pixels for sensing green light and B pixels for sensing blue light. For each R, G, and B pixels is disposed a respective signal conversion device so that an electric signal is generated when light of wavelength (color) corresponding to each pixel is incident. For example, color image is detected in such a manner that when the R pixel is irradiated with the red light, the R pixel reacts to generate an electric signal, but when the R pixel is irradiated with the blue light or the green light, the electric signal is not generated. FIG. 4 is a graph showing quantum efficiency according to wavelengths of a color CMOS sensor used in the eye-examining apparatus according to the present invention. As shown in FIG. 3 and FIG. 4, the color CMOS sensor used in the present invention has B pixels having excellent quantum efficiency for blue light having a wavelength of about 470 nm, G pixels having excellent quantum efficiency for green light having a wavelength of about 550 nm and R pixels having excellent quantum efficiency for red light having a wavelength of about 600 nm or more. The R, G and B pixels of the color CMOS sensor are excellent in sensitivity to red light R, green light G, and blue light B in the visible light range. However, for infrared light having a wavelength of 700 nm or more, the sensitivity (quantum efficiency) is changed depending on R, G and B pixels. For example, as shown in FIG. 4, when light of 770 nm wavelength, which is commonly used for infrared light, is irradiated, the quantum efficiency of the B pixel is only 13%, but the quantum efficiency of the R pixel is 33%. That is, even if the same infrared light is incident, the quantum efficiency may be changed depending on the R, G, and B pixels, so that the signal (image) detected by the R, G, and B pixels may become unstable.

On the other hand, in a conventional infrared optical system (keratometry channel) using infrared measuring light, a monochromatic sensor is used instead of a color sensor. FIG. 5 is a graph showing the quantum efficiency of the conventional monochromatic sensor. As shown in FIG. 5, typical monochromatic sensors for sensing infrared light exhibits excellent quantum efficiency for infrared light at wavelengths from 700 to 800 nm. Therefore, like the conventional eye-examining apparatus, if monochromatic sensor 14 is used for the infrared optical system 10 (keratometry channel) which measures the cornea using the infrared measuring light of a wavelength of 770 nm and the color sensor 44 is used for the observing optical system 40, that is, when a separate sensor is used for each optical system (optical channel), both infrared light image and visible light image can be stably obtained. However, this causes a complicated structure of the optical system as described above.

On the other hand, in the eye-examining apparatus according to the present invention, it is preferable that infrared light having the same or similar sensitivity (quantum efficiency) to the R, G, and B pixels of the color CMOS sensor is used as infrared light for the cornea measurement. As shown in FIG. 4, when the wavelength of infrared light is about 810 nm or more, preferably about 850 nm or more, more preferably about 900 nm or more, and about 1050 nm or less, preferably about 1000 nm or less, more preferably about 950 nm or less, the sensitivity (quantum efficiency) of the R, G, and B pixels of the color CMOS sensor becomes substantially the same. Therefore, even when the color CMOS sensor is used, the image of the infrared light of the infrared light source 12, formed on the front of the examinee's eye can be stably detected. That is, when from the infrared light source 12 to the examinee's eye 5 is irradiated the infrared light having a wavelength of about 810 nm or more, preferably about 850 nm or more, more preferably about 900 nm or more, and having a wavelength of 1050 nm or less, preferably 1000 nm or less, more preferably 950 nm or less, the R, G, and B pixels of the color CMOS sensor have the same sensitivity as the monochrome sensor so that the color CMOS sensor can be used as sensor for detecting the infrared light image. The image detector 64 in the present invention has uniform detection sensitivity to the visible light and the infrared light having a wavelength of 810 nm or more. There are disadvantages that when the wavelength of the infrared light is too small, the R, G and B pixels of the color CMOS sensor can generate different signals, and when the wavelength of the infrared light is too high, the sensitivity of the R, G and B pixels is overall reduced. That is, in the present invention, the color CMOS sensor used as the image detector 64 has a different quantum efficiency depending on R, G, and B pixels for light having a wavelength of less than about 810 nm while the quantum efficiency of the color CMOS sensor is substantially the same according to the R, G, and B pixels for light having a wavelength of about 810 nm or more.

In the case of detecting infrared light with the color CMOS sensor, when the visible light is irradiated to the color CMOS sensor, a signal irrelevant to infrared light may be detected from the R, G, and B pixels since the sensitivities of the R, G, and B pixels of the color CMOS sensor to visible light are different from each other. Accordingly, in the present eye-examining apparatus, it is preferable that for detecting the infrared light, in front of the image detector 64 is installed the visible light blocking filter 66 so that visible light or near infrared light having a wavelength of less than 810 nm, preferably less than 850 nm, more preferably less than 900 nm is cut off and visible light cannot be delivered to the image detector 64.

Referring again to FIG. 2, the eye-examining apparatus according to the present invention may further includes the chart optical system 20, the refractive power measuring optical system 30, and the like.

As the chart optical system 20 may be used a conventional optical system for irradiating a chart to an examinee's eye. The chart optical system 20 includes an illumination source 22 for emitting illumination light, a chart 24 to which the illumination is transmitted to produce a chart image for fixing the eyes thereon, an adjustment lens 26 for adjusting a focal distance of the image produced in the chart 24, optical elements of a reflective mirror 28, a beam splitter 68, relay lens 29, for reflecting and transmitting the image generated in the chart 24 to the eye. Here, the chart image formation on the retina of the eye 5 is performed by adjusting the distance between the adjustment lens 26 and the chart 24 by moving the adjustment lens 26 and/or the chart 24. In operation of the chart optical system 20, from the illumination source 22 is emitted the white illumination light which in turn passes through the chart 24, thereby to generate a chart image for fixing the eyes 5 on the chart and for releasing the adjustment force of the eyes. The image generated in the chart 24 is passed through the adjustment lens 26, the relay lens 29, the reflection mirror 28 and the splitter 68 to be delivered to and focused on a retina of the examinee's eye 5. After the chart image is formed on the examinee's eye, the chart 24 is moved so that the chart image is not focused on the focus position of the examinee's eye 5, thereby releasing the adjustment force of the examinee's eye 5. When the adjustment force of the examinee's eye 5 is lost, the refractive power of the eye 5 is measured using the refractive power measuring optical system 30.

As the refractive power measuring optical system 30 may be used a conventional optical system for measuring the refractive power of the examinee's eye 5. The refractive power measuring optical system 30 includes a measuring light source 32 for irradiating infrared light for measuring the refractive power to the eye 5 and a refraction image detector 34 for detecting the signal light formed by the measuring light reflected from the retina of the eye 5 and refracted at the eye 5. The refractive power of the eye 5 can be calculated from the image of the signal detected by the refractive image detector 34. For example, the refractive power measuring optical system 30 includes a ring mask 52 for transmitting the measuring light irradiated from the measuring light source 32 in form of a ring, optical elements of a focusing lens 35, a relay lens 54, a hole mirror 56, a beam splitter 68, a reflecting mirror 57, an objective lens 61, and the like, for focusing, transmitting, or reflecting the ring-shaped measuring light formed in the ring mask 52 onto the retina of the eye 5, and optical elements of a reflection mirror 58, a relay lens 39, and the like, for transmitting the signal light reflected from the retina of the examinee's eye to the refractive image detector 34. As the image detector 34 a conventional infrared (IR) detection CMOS sensors can be used. In operation, from the measuring light source 32 is emitted a refractive power measuring light. The measuring light of ring shape is irradiated to the examinee's eye 5 through the ring mask 52 and focused on the top of the cornea of the examinee's eye 5. The measuring light forms a ring-shaped image on the retina of the examinee's eye 5 with a predetermined size, and the ring-shaped image (signal light) reflected by the retina of the examinee's eye 5 is refracted at the cornea. The refracted ring-shaped image is detected by the refraction image detector 34. The refractive power of the examinee's eye 5 can be calculated from the size and shape of the detected ring-shaped image.

According to the present invention, both the infrared optical system and the observation optical system can be observed using single one image detector 64. Therefore, the optical system of the eye-examining apparatus is simplified, and the number of components and the product size thereof can be reduced.

The invention claimed is:

1. An eye-examining apparatus having a visible-infrared integrated optical system, comprising:
    an infrared light source for irradiating a cornea of an examinee's eye with infrared light of a predetermined shape;
    a visible light source for irradiating the examinee's eye with visible light;
    an image detector for detecting an image of the infrared light which is irradiated from the infrared light source and reflected from the cornea of the examinee's eye and for detecting an image of the visible light which is irradiated from the visible light source and reflected from the examinee's eye; and
    a visible light blocking filter configured to be selectively inserted in an optical path of the visible light and the infrared light between the examinee's eye and the image detector for blocking the visible light,
    wherein wavelength of the infrared light irradiated from the infrared light source is 810 nm or more and 1050 nm or less, and
    wherein the image detector is a color sensor for selectively detecting a visible light image of the examinee's eye and an infrared light image reflected from the cornea; and the color CMOS sensor comprises R, G and B pixels for detecting red light R, green light G and blue light B, respectively, and
    the R, G and B pixels of the color CMOS sensor have substantially same sensitivity to the infrared light of wavelength of 810 nm or more and 1050 nm or less so that the color CMOS sensor is used as sensor for detecting an image of the infrared light.

2. The eye-examining apparatus of claim 1, wherein the integrated optical system detects the image of the infrared light reflected by the cornea of the examinee's eye to measure corneal configuration of the examinee's eye and observes a shape of the examinee's eye from the image of the visible light by the examinee's eye.

3. The eye-examining apparatus of claim 1, wherein when infrared light is irradiated from the infrared light source, the visible light blocking filter is inserted into a path of the infrared light to cut off the visible light, and the image of the infrared light reflected by the cornea of the examinee's eye is detected by the image detector, and when visible light is emitted from the visible light source, the visible light blocking filter is removed from a path of the visible light and the image of the visible light of the examinee's eye is detected by the image detector.

4. The eye-examining apparatus of claim 1, wherein the visible light blocking filter cuts off visible light or near infrared light having wavelength of less than 810 nm.

5. The eye-examining apparatus of claim 1, further comprising a chart optical system, the chart optical system comprising: an illumination source for emitting illumination light; a chart to which the illumination is transmitted to produce a chart image for fixing the eyes thereon; an adjustment lens for adjusting a focal distance of the image produced in the chart; and optical elements for reflecting and transmitting the image generated in the chart to the eye.

6. The eye-examining apparatus of claim 1, further comprising a refractive power measuring optical system, the refractive power measuring optical system comprising: a measuring light source for irradiating infrared light for measuring the refractive power to the eye; and a refraction image detector for detecting a signal light formed by the measuring light reflected from a retina of the eye and refracted at the eye.

* * * * *